(12) United States Patent
He et al.

(10) Patent No.: US 6,234,956 B1
(45) Date of Patent: May 22, 2001

(54) MAGNETIC ACTUATION URETHRAL VALVE

(76) Inventors: Hongping He; Ming He, both of 5715 Greenhorn Mountain Ct., Bakersfield, CA (US) 93313

( * ) Notice: Subject to any disclaimer, the term of this patent is extended or adjusted under 35 U.S.C. 154(b) by 0 days.

(21) Appl. No.: 09/373,020

(22) Filed: Aug. 11, 1999

(51) Int. Cl.[7] .................................................. A61F 2/02
(52) U.S. Cl. ................................................................ 600/30
(58) Field of Search ........................ 600/29, 30; 128/899, 128/DIG. 25

(56) References Cited

U.S. PATENT DOCUMENTS

| 5,380,268 | * | 1/1995 | Wheeler | 600/30 |
| 5,634,878 | * | 6/1997 | Grundei et al. | 600/30 |
| 5,713,877 | * | 2/1998 | Davis | 600/29 |
| 5,762,599 | * | 6/1998 | Sohn | 600/30 |
| 5,989,288 | * | 11/1999 | Pintauro et al. | 600/30 |

* cited by examiner

*Primary Examiner*—John P. Lacyk
*Assistant Examiner*—Joseph A. Cadugan
(74) *Attorney, Agent, or Firm*—Raymond Y. Chan; David & Raymond Patent Group

(57) ABSTRACT

A magnetic actuation urethral valve is adapted for inserting into the urethra of a patient who suffering from urinary incontinence in order to recover control of urine flow. The valve member is driven by a magnet rotor which is magnetically actuated by a rotating magnetic field generated from a controller outside the body. There is also an actuation device for the user to discharge by inserting an indwelling catheter into the valve in case the valve does not work for any reason.

14 Claims, 4 Drawing Sheets

MAGNETIC ACTUATION URETHRAL VALVE

BACKGROUND OF THE PRESENT INVENTION

1. Field of the Present Invention

The present invention relates to urethral valves, and more particularly to a magnetic actuation urethral valve adapted for inserting into the urethra of a patient who suffering from urinary incontinence in order to recover control of urine flow.

2. Description of Related Arts

Urinary incontinence is a common and serious problem that may be caused by old age, some forms of neurological dysfunction or injuries, or prostate and bladder surgeries. Such problem is hard to treat or, generally, incurable. Patients suffering from this problem not only may experience discomfort and embarrassment, but also may lose some normal human activities.

Many efforts have been taken to solve this problem. Use of indwelling catheters and associated bags often leads to infections of the bladder because the catheter provides a direct passage to microorganisms into the human body. Use of diapers is uncomfortable and embarrassing. Use of artificial urethral sphincters needs surgical implantation that is expensive, complicated, and has a low success rate, sometimes leading to serious complications. Use of various kinds of urethral valve for non-surgical insertion into the urethra is a simple, low-cost, and easy-to-accept way to recover urinary continence.

U.S. Pat. Nos. 4,909,785 and 5,112,306 introduce a device for valving urine involving a flexible tubular body with a drainage canal therethrough, which includes collapsible means for blocking the passageway of urine. It is manually actuated to an open position by means of pressing the flexible valve body. It also includes means for closing the valve automatically after a period delay in which allows voiding of the bladder. The structure of this device is complicated while its size is considerably large.

There are a few different types of magnetic actuation urethral valves such as U.S. Pat. Nos. 3,812,841, 5,004,454, and 5,140,999. These devices have some basic properties in common. They are all magnetic in nature and respond to a magnetic fields generated at the exterior of the body. They all need a bias from a spring to maintain their closed position. Their differences are present mainly in the forms of the interactions between the magnetic valve and the controlling magnetic field.

In U.S. Pat. No. 3,812,841, the valve member is pulled directly by external force. The magnet in the valve must be large enough in size to get enough pulling force from the controlling magnetic field against the bias to open the valve. Due to the weak pulling force from direct attraction, it does not work reliably and increases the possibility of malfunction of the unit and consequential repair or replacement. Furthermore, its physical size presents extreme difficulties in insertion and removal.

U.S. Pat. No. 5,004,454 is much simpler and smaller in size then U.S. Pat. No. 3,812,841. Instead of using direct pulling force to open the valve member, it takes the mechanical advantage by using a lever to gain more force to open the valve member than the direct attraction. Because of the efficiency of this mechanism, the size of the magnet in the valve can be reduced. The lever is the valve member itself in a special shape inside the valve body. The valve body limits the range of the lever and the valve that is actuated is quite small, so that urine flow is reduced to a trickle.

U.S. Pat. No. 5,140,999 is very similar to U.S. Pat. No. 5,004,454. The main progress made by U.S. Pat. No. 5,140,999 is that there is an actuator rod which extends out of the valve body and into the bladder, providing greater torque and range for opening the valve. One problem of this design is that the valve might leak when the patient moves tremendously such as running or jumping due to the vibration of relatively long actuator rod with a magnet on its top. Another problem is the possibility of formation of bladder stones caused by a foreign object, which is the extending actuator rod inside the bladder.

SUMMARY OF THE PRESENT INVENTION

The main objective of the present invention is to provide a magnetic actuation urethral valve adapted for inserting into the urethra of a patient who suffering from urinary incontinence in order to recover control of urine flow, wherein the valve member is driven by a magnet rotor which is magnetically actuated by a rotating magnetic field generated from a controller outside the body.

Another objective of the present invention is to provide a magnetic actuation urethral valve which further comprises an actuation device for the user to discharge by inserting an indwelling catheter into the valve in case the valve does not work for any reason.

Accordingly, a magnetic actuation urethral valve according to the present invention is adapted for introduction into a portion of an urethra of a patient suffering from lesions or disorders of the urethra, the prostate or the urinary sphincters. It has a tubular body with a valve member at is proximal end opening to the bladder and a magnet rotor in its roomy central cavity.

The movable valve member connects to the magnet rotor with an actuation axle which is supported by a control nut. The magnet rotor is actuated by a rotating magnetic field generated from a magnetic controller outside of the body and the rotational motion of the magnet rotor is translated into linear motion by the actuation axle and the control nut to push the valve member open to the bladder or pull the valve member back to its closed state.

When the rotor turns clockwise, the movable valve member moves away from the valve seat to its open position through which urine can be released from the bladder. When the magnet rotor turns counterclockwise, the valve member moves back to its normal closed position and shuts off the passageway of urine.

This mechanism, which has the same principle as that of a car jack, gains much greater force for the linear motion of valve member from the force of rotational motion of the rotor. In other words, the force driving the valve member is much greater than the force driving the magnet rotor from the direct interaction between the magnet rotor and the controlling magnetic field.

To get strong force is very important to make sure the operation of the valve can be reliably performed and the size of the valve body can be reduced. That is the basic point to make this valve reliable, and easy to install or remove.

The limited range of the thread area of the actuation axle and the control nut are designed to prevent the valve from getting stuck when the threaded hole and the control nut is over-tightened. The springs at each side of the control nut are for the purpose of being able to secure the threaded portion of the actuation axle going back into the control nut after the threaded portion runs out of the control nut in both directions.

The present invention further comprises an actuation device for the user to discharge the urine in the bladder by inserting a catheter into the valve in case the valve is not working properly for any reason. The nut, which is normally urged to the valve body by a spring, can be moved axially in the valve body. Since these four members of the valve member, the actuation axle, the control nut, and the magnet rotor, are assembled as a firm assembly, the whole assembly can be moved in axial direction in the valve body.

In the case of emergency, user can insert a catheter into the distal end of the valve body through the urethra to push the magnet rotor. The assembly is moved toward the proximal end and the spring is compressed. As a result, the valve member moves to the open position and the urine in the bladder is released. When the catheter is removed, the compressed spring urges the assembly back to normal position and the valve is closed.

DETAILED OF THE PREFERRED EMBODIMENT

Figure 1:
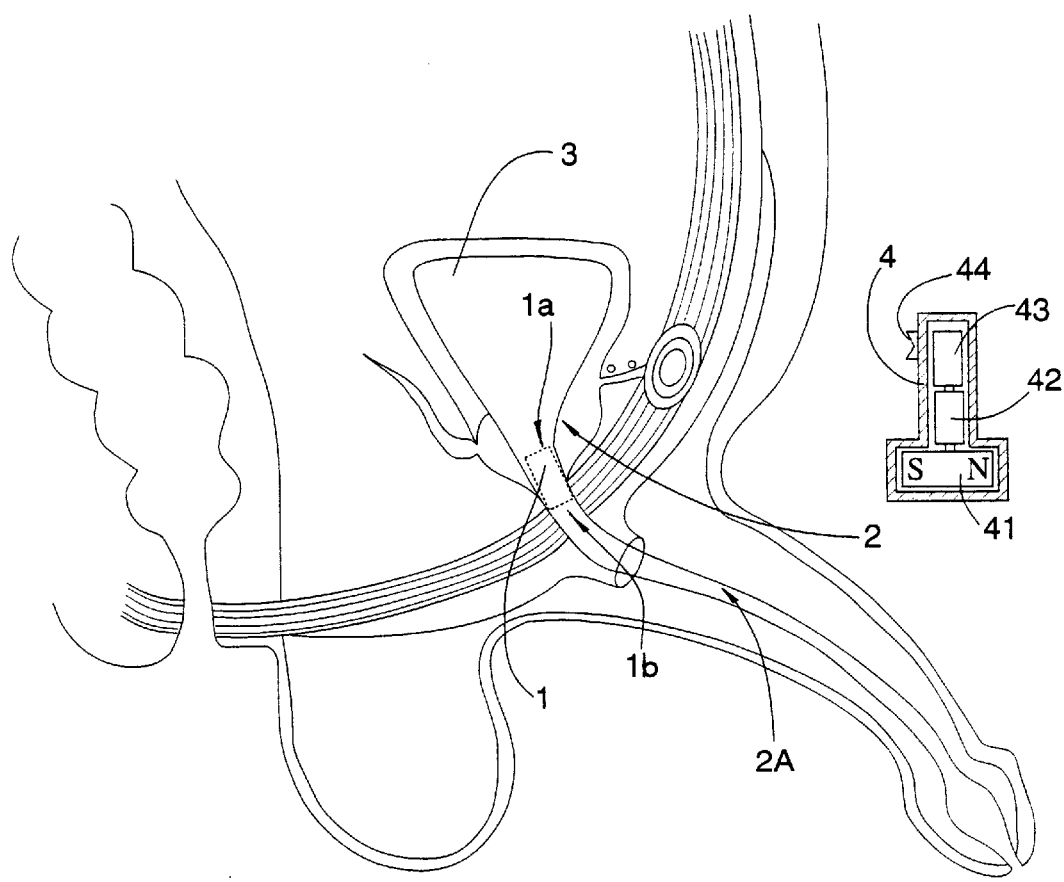
FIG. 1 is a schematic view illustrating a magnetic actuation urethral valve, according to a preferred embodiment of the present invention, which is placed in the prostate portion of the male urethra with the proximal end opening to the bladder, wherein the controller turns to produce a rotating magnetic field to drive the magnetic urethral valve open and close.
Figure 2:
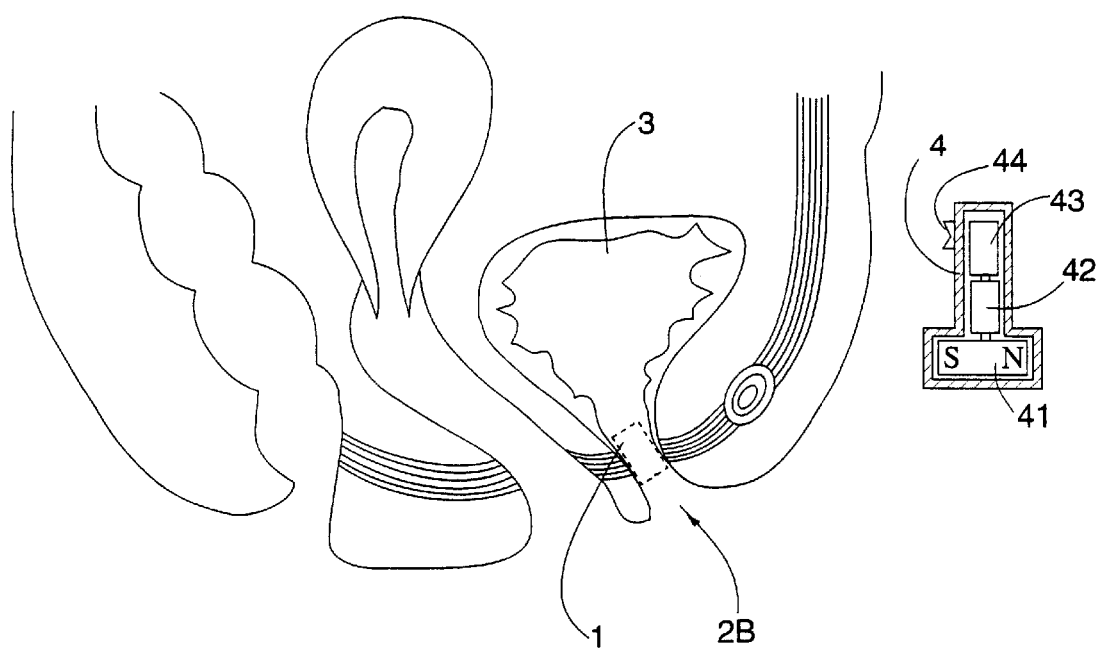
FIG. 2 is a schematic view illustrating the magnetic actuation urethral valve placed in the female urethra according to the above preferred embodiment of the present invention.

Referring FIG. 1 of the drawings, a magnetic actuation urethral valve 1 according to a preferable embodiment of the present invention is placed in the prostate portion 2 of a male urethra 2A with a proximal end 1*a* thereof opening to a bladder 3, wherein a magnetic controller 4 turns to produce a rotating magnetic field to drive the magnetic actuation urethral valve 1 between an open position and a close position. FIG. 2 illustrates where the magnetic actuation urethral valve 1 should be placed in a female urethra 2B.

As shown in FIGS. 1 and 2, the magnetic controller 4 comprises a strong permanent magnet 41 and a geared DC motor 42. The DC motor 42 turns the magnet 41 clockwise or counterclockwise by exchanging the positive and negative connections to a power source 43 through a switch 44 of the controller 4, thus produces the rotation of the controlling magnetic field in both directions to drive the magnet rotor, which opens the valve and lets out the urine or shuts it. The gears are for reducing the turning speed of the motor.

Referring to FIGS. 3 to 6, the magnetic actuation urethral valve 1 according to the preferable embodiment of the present invention has a shape of lumenal cylinder and has a proximal end 1*a* and a distal end 1*b*. The proximal end 1*a* forms an opening to the bladder 3 while the distal end 1*b* opens to the urethra 2A, 2B.

The magnetic actuation urethral valve 1 comprises a valve member 10, a valve body 20 and an actuation device 30 for selectively spacing out the valve member 10 and the valve body 20 from each other so as to let the urine flow through the valve body 20 when it is opened; then the urine is discharged.

Figure 3:
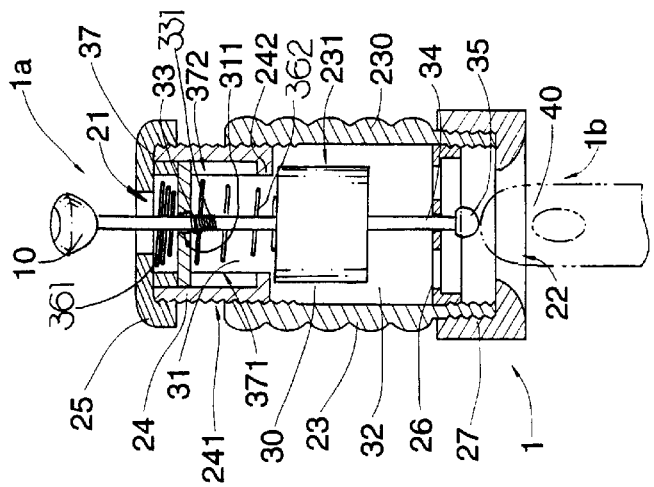
FIG. 3 is partial sectional view of the magnetic actuation urethral valve in close position according to the above preferred embodiment of the present invention.

Referring to FIGS. 3 to 6, the valve body 20 of the magnetic actuation urethral valve 1 having a valve opening 21 at the proximal end 1*a* and an exit opening 22 at the distal end 1*b*, wherein the proximal valve opening 21 has a size smaller than a size of the valve member 10 so as to enable the valve member 10 sifting on the proximal valve opening 21 to shut off the valve body 20 to stop any urine passing through the valve body, as shown in FIG. 3.

The actuation device 30 comprises a control nut 31, a magnet rotor 32 rotatably disposed inside the valve body 20 and adapted to be driven to rotate by the magnetic controller 4 as shown in FIGS. 1 and 2, an actuation axle 33 having a first end penetrating through the valve opening 21 and connecting to the valve member 10 and a second end coaxially connected to the magnet rotor 32, and a manual switch axle 34 distally extended from the magnet rotor 32 towards the exit opening 22 to connect with a switch button 35.

The control nut 31, which is non-roatably positioned between the valve opening 21 (i.e. the valve member 10) and the magnet rotor 32, has a central threaded hole 311 provided therethrough. The actuation axle 33, which penetrates through the threaded hole 311 of the control nut 31, has a threaded portion 331 adapted for screwing with the thread hole 311.

As shown in FIGS. 1 to 3, the user may use the magnetic controller 4 to drive the magnet rotor 32 to rotate in, for example, counterclockwise direction. The rotating magnet rotor 32 then drives the actuation axle 33 to rotate in clockwise direction so as to drive the thread portion 331 of the actuation axle 33 to move axially towards the distal end 1*b*. Therefore, the valve member 10 is pulled by the actuation axle 33 to shut off the valve opening 21 to close the valve body 20.

Figure 4:
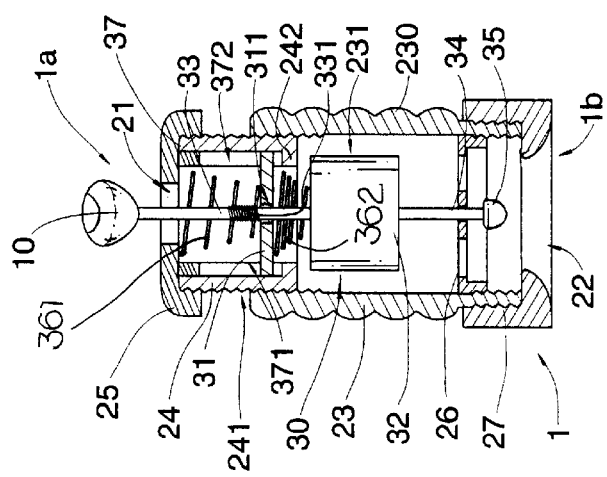
FIG. 4 is partial sectional view of the magnetic actuation urethral valve in open position according to the above preferred embodiment of the present invention.

As shown in FIGS. 1, 2 and 4, the user may use the magnetic controller 4 to drive the magnet rotor 32 to rotate in clockwise direction. The rotating magnet rotor 32 then drives the actuation axle 33 to rotate in an opposite direction to drive the thread portion 331 of the actuation axle 33 to move axially towards the proximal end 1*a*. Therefore, the valve member 10 is pushed by the actuation axle 33 to move away from the valve opening 21 to open the valve body 20.

When the magnetic actuation urethral valve 1 of the present invention is operated from an open position (as shown in FIG. 4) to a normal close position (as shown in FIG. 3), the controlling magnetic field induced by the magnetic controller 4 outside the user's body turns the magnet rotor 32 counterclockwise. The threaded portion 331 of the actuation axle 33 rotates through the threaded hole 311 of the control nut 31; as a result, the actuation axle 33 pulls the valve member 10 towards the valve opening 21 to shut off the valve opening 21 of the valve body 20 so as to block the passageway of urine. If the control nut 31 was fixed, then, when the magnet rotor 32 continues to rotate, the valve member 10 would be tightened more and more until it gets stuck from over-tightening; then, the user would need to use greater force to re-open the valve opening 21. But there is still a possibility of not been able to open valve opening 21 at all.

According to the present invention, in order to prevent the abovementioned from happening, the control nut 31 is designed to equipped with the thread portion 331 of the actuation axle 33, that not only can guide the linear motion of the actuation axle 33 but also can prevent the actuation axle 33 from being over-rotated. As shown in FIG. 3, during the close position, the threaded portion 331 of the actuation axle 33 is just downwardly passed through the thread hole 311 and positioned underneath the control nut 31. At that moment, even the user continues to use the magnetic controller 4 to induce the magnet rotor 32 to drive the actuation axle 33 to rotate, the valve member 10 will only be freely to rotate and the actuation axle 33 is unable to drive the valve member 10 to move more towards the valve opening 21 so as to prevent the valve member 10 from over tight condition.

According to the preferable embodiment of the present invention, as shown in FIGS. 3 to 6, the valve body 20 comprises a valve housing 23, a connecting sleeve 24, a valve seat 25, a retainer bearing 26, and a cover cap 27.

The valve housing 23 has a wavy exterior surface 230 adapted to more firmly mount within urethra and an interior chamber 231 to receive the magnet rotor 32 therein. The connecting sleeve 24 has a threaded exterior surface 241 for screwing to a proximal end of the valve housing 23, and a ring shaped supporting shoulder 242 radially and inwardly extended from a bottom end thereof The valve seat 25 which has a U-shaped cross section is coaxially screwed to the connecting sleeve 24. The valve seat 25 has a center hole functioned as the valve opening 21, wherein the diameter of the valve opening 21 must be smaller than the maximum diameter of the valve member 10. The retainer bearing 26 is screwed to affixed at a distal end portion of the valve housing 23 to prevent the magnet rotor 32 from falling out. A plurality of urine holes 261 is formed on the retainer bearing 26 for enabling the urine to flow through. The cover cap 27, which is secured to a distal end of the valve housing 23 for a special instrument to place and/or remove the urethral valve 1, has a central opening functioned as the exit opening 22 of the urethral valve 1.

The valve member 10 is a semi-spherical surface fitting onto the valve seat 25. The actuation device 30 further comprises a first spring 361 and a second spring 362 which maintain certain pressures between the valve member 10 and the valve seat 25 as well as control the movement of the control nut 31. The actuation device 30 also comprises a guiding sleeve 37 fittingly installed within the connecting sleeve 24 and supported by the supporting shoulder 242. Two opposing guiding slots 371, 372 are longitudinally formed on the guiding sleeve 37. The control nut 31 has two guider ends 312, 313 projected from two ends thereof, wherein the two guider ends 312, 313 are slidably fitted in the two guiding slots 371, 372 respectively so as to enable the control nut 31 to slide axially within the guiding sleeve 37.

As mentioned above, the control nut 31, cooperating with the threaded portion 31 of the actuation axle 33, prevents themselves from getting stuck when it is over-tightened while operating the urethral valve 1 from open to closed or from closed to open positions.

The length of the threaded exterior surface 241 of the connecting sleeve 24 determines the range of movements for the control nut 31 and the valve member 10. Moreover, the threaded portion 331 of the actuation axle 33 and the control nut 31 cooperating together converts the rotational movement of the magnet rotor 32 into a linear pushing movement to drive the valve member 10 open and close.

Figure 5:
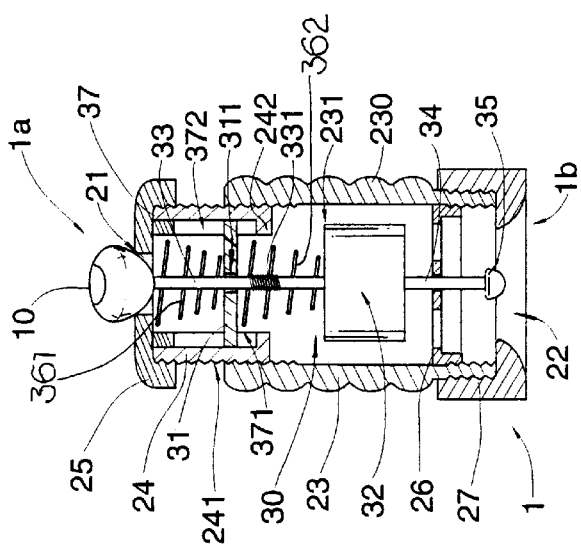
FIG. 5 is partial sectional view of the magnetic actuation urethral valve in the position of emergency open position, opened by inserting a catheter, according to the above preferred embodiment of the present invention.

The retainer bearing 26 has a center hole 262 having a diameter equal to or slightly larger than the diameter of the switch axle 34 so as to enable the switch axle 34 rotatably passing through. The switch button 35 is extended below the retaining bearing 26 for the purpose of pushing the valve member 10 upwards to open valve opening 21 with a catheter 40, as shown in FIG. 5, in the case of any problems with the urethral valve 1 that disables its ability to work properly for any reason.

Figure 6:
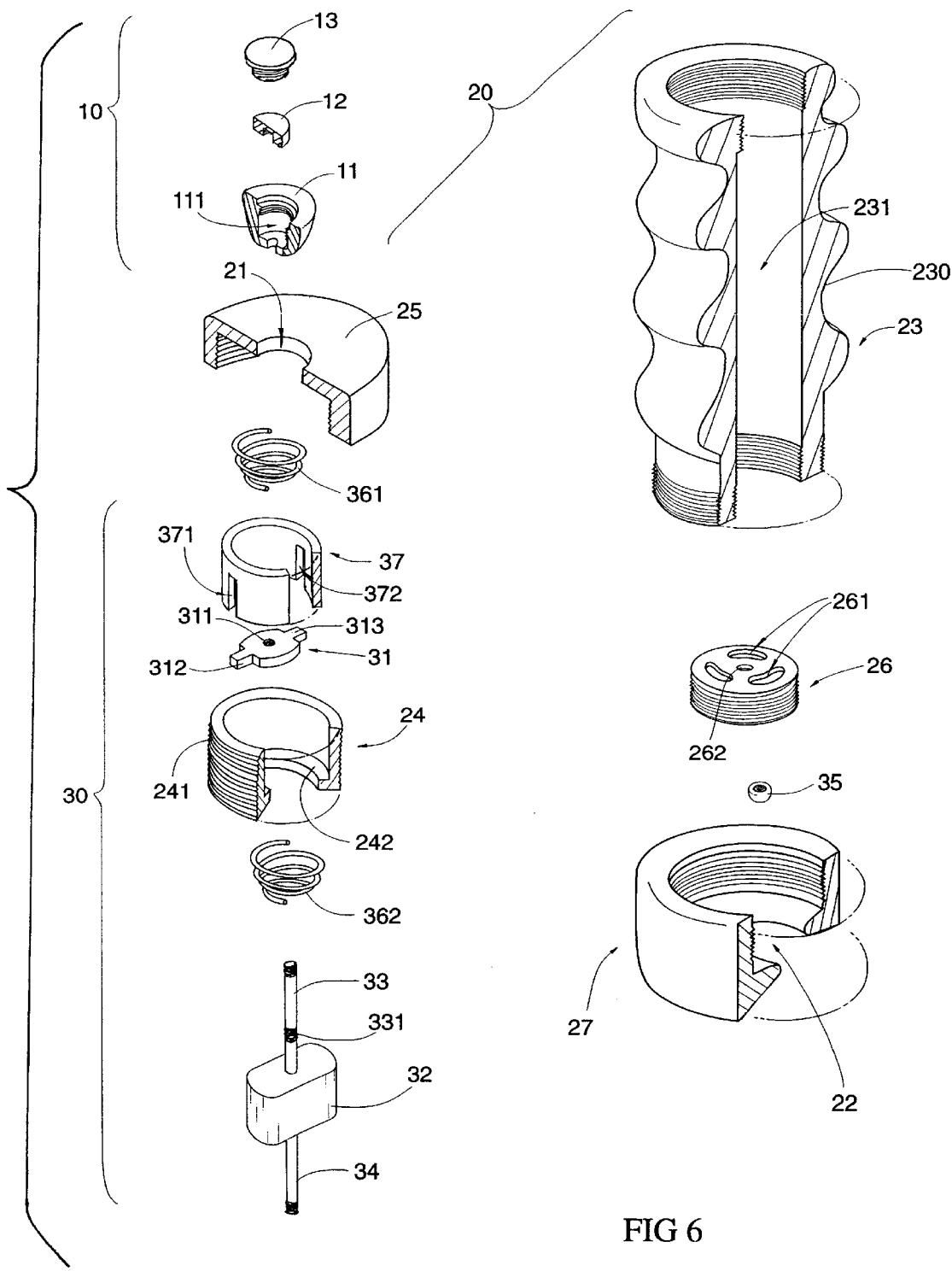
FIG. 6 is an exploded view of the magnetic actuation urethral valve according to the above preferred embodiment of the present invention.

As shown in FIG. 6, the valve member 10 comprises a valve head 11 having a step hole 111 therein, a head nut 12 is disposed within the step hole 111 for tightly screwed onto the first end of the actuation axle 33, and a head cover 13 covering the step hole 111 (i.e. the head nut 12) by screwing therein. It is designed to fix the actuation axle 33 as well as to allow the actuation axle 33 to rotate inside the valve member 10 freely. Without such structure, the valve member 10 would rub against the valve seat 25 and engender a lot of friction when the actuation axle 33 rotates the valve member 10, increasing the force needed for the urethral valve 1 to open or close.

As mentioned above, the control nut 31 is designed to be able to glide along the guiding slot 371, 372, and the length of threaded portion 331 is limited so as to limit the sliding range of the control nut 31. Thus, although the urethral valve 1 is closed, and the magnet rotor 32 is still rotating and driving the actuation axle 33, the control nut 31 will be pushed upwards until it is out of the threaded portion 331 area, it will not move upwards further because it has just lost its driving force from threaded portion 331, even if it is still turning; nothing will happen, and so prevents the valve member 10 getting stuck from over tightening. At this time, the first spring 361 is compressed between control nut 31 and valve seat 25. The first spring 361 pushes through the control nut 31 and the actuation axle 33, pulling valve member 10 toward valve seat 25, and maintains certain pressure for the normal closed state.

When the urethral valve 1 needs to be opened, we can use the rotating magnetic field by operating the magnetic controller 4 outside the body to drive the magnet rotor 32 to turn clockwise. Since the first spring 361 is compressed between the control nut 31 and the valve seat 25, the first spring 361 pushes the control nut 31 to the threaded portion 331 of the actuation axle 33. As a result, the threaded portion 331 screws into the threaded hole 311 of the control nut 31, and the control nut 31 starts moving downwards and compresses the second spring 362. At the same time actuation axle 33 moves upward, pushing the valve member 10 to open position, as shown in FIG. 4, enabling the urine to pass through the urethral valve 1 to the urethra. If the actuation axle 33 continues to rotate, threaded portion 331 will move upwards out of the control nut 31, once again loosing the driving force. This also prevents it from getting stuck in the opposite direction. The compressed second spring 362 pushes the control nut 31 upwards, ensuring that when the valve needs to be closed, threaded portion 331 of the actuation axle 33 can once again turn through the control nut 31.

If, for any reason the valve is not functioning properly with the controller, the patient himself/herself can use the catheter 40 to push the urethral valve 1 open, as shown in FIG. 5, precluding the retention of urine. As the actuation device 30 and the valve member 10 are assembled into a solid unit, when the catheter 40 pushes the switch button 35, the valve member 10 would be pushed to open position, as shown in FIG. 5, and then the urine can flow directly from the bladder through the urethral valve 1 to the catheter 40 and out of the body. When the valve is opened, the first spring 361 is compressed; when the catheter 40 is removed, the valve member 10 will close itself because of the springiness of the first spring 361.

What is claimed is:

1. A magnetic actuation urethral valve, comprising:
    a valve member:
    a valve body having a valve opening at a proximal end thereof and an exit opening at a distal end thereof, wherein said valve opening has a size smaller than a size of said valve member so as to enable said valve member sitting on said valve opening to shut off said valve body, wherein said valve body comprises a valve housing, a connecting sleeve, a valve seat, a retainer bearing, and a cover cap, said valve housing having an interior chamber, said connecting sleeve connecting to a proximal end of said valve housing, and a ring shaped supporting shoulder radially and inwardly extended from a bottom end thereof, said valve seat which has a U-shaped cross section is coaxially connected to said connecting sleeve, said valve seat having a center hole functioned as said valve opening, said retainer bearing being affixed at a distal end portion of said valve housing, a plurality of urine holes being formed on said retainer bearing, said cover cap being secured to a distal end of said valve housing and having has a central opening functioned as said exit opening; and
    an actuation device for selectively spacing out said valve member and said valve body from each other, wherein said actuation device comprises a control nut, a magnet rotor rotatably disposed inside said interior chamber of said valve housing of said valve body and adapted to be driven to rotate by a magnetic controller, and an actuation axle having a first end penetrating through said valve opening and connecting to said valve member and a second end coaxially connected to said magnet rotor; wherein said control nut is positioned between said valve opening and said magnet rotor and has a central threaded hole so as to enable said actuation axle to penetrate therethrough, and that said actuation axle has a threaded portion adapted for screwing with said thread hole;
    whereby by means of said magnetic controller, said magnet rotor is able to be driven to rotate in one direction, said rotating magnet rotor driving said actuation axle to rotate so as to drive said thread portion of said actuation axle to move axially towards said distal end, so that said valve member is pulled by said actuation axle to shut off said valve opening to close said valve body, furthermore when said magnet rotor is driven by said magnetic controller to rotate in opposite direction, said rotating magnet rotor drives said actuation axle to rotate to drive said thread portion of said actuation axle to move axially towards said proximal end, so that said valve member is pushed by said actuation axle to move away from said valve opening to open said valve body.

2. A magnetic actuation urethral valve, as recited in claim 1, wherein said actuation device further comprises a first spring and a second spring which maintain certain pressures between said valve member and said valve seat as well as control movement of said control nut, and a guiding sleeve fittingly installed within said connecting sleeve and supported by said supporting shoulder, wherein two opposing guiding slots are longitudinally formed on said guiding sleeve, said control nut having two guider ends projected from two ends thereof, wherein said two guider ends are slidably fitted in said two guiding slots respectively so as to enable said control nut to slide axially within said guiding sleeve.

3. A magnetic actuation urethral valve, as recited in claim 2, wherein said actuation device further comprises a manual switch axle distally extended from said magnet rotor towards said exit opening to connect with a switch button, wherein said retainer bearing has a center hole to enable said switch axle rotatably passing through, and said switch button is extended below said retaining bearing for pushing said valve member upwards to open said valve opening with a catheter or the like.

4. A magnetic actuation urethral valve, as recited in claim 3, wherein said valve member comprises a valve head having a step hole therein, a head nut disposed within said step hole for tightly screwed onto said first end of said actuation axle, and a head cover covering said step hole by screwing therein, thus allowing said actuation axle to rotate inside said valve member freely.

5. A magnetic actuation urethral valve, as recited in claim 2, wherein said valve member comprises a valve head having a step hole therein, a head nut disposed within said step hole for tightly screwed onto said first end of said actuation axle, and a head cover covering said step hole by screwing therein, thus allowing said actuation axle to rotate inside said valve member freely.

6. A magnetic actuation urethral valve, as recited in claim 1, wherein said valve member comprises a valve head having a step hole therein, a head nut disposed within said step hole for tightly screwed onto said first end of said actuation axle, and a head cover covering said step hole by screwing therein, thus allowing said actuation axle to rotate inside said valve member freely.

7. A magnetic actuation urethral valve, comprising:
    a valve member:
    a valve body having a valve opening at a proximal end thereof and an exit opening at a distal end thereof, wherein said valve opening has a size smaller than a size of said valve member so as to enable said valve member sitting on said valve opening to shut off said valve body; and
    an actuation device for selectively spacing out said valve member and said valve body from each other, wherein said actuation device comprises a control nut, a magnet rotor rotatably disposed inside said valve body and adapted to be driven to rotate by a magnetic controller, and an actuation axle having a first end penetrating through said valve opening and connecting to said valve member and a second end coaxially connected to said magnet rotor, wherein said control nut is positioned between said valve opening and said magnet rotor and has a central threaded hole so as to enable said actuation axle to penetrate therethrough, and that said actuation axle has a threaded portion adapted for screwing with said thread hole, wherein said actuation device further comprises a first spring and a second spring which maintain certain pressures between said valve member and said valve body as well as control movement of said control nut, and a guiding sleeve fittingly installed within said valve body, wherein two opposing guiding slots are longitudinally formed on said guiding sleeve, said control nut having two guider ends projected from two ends thereof, wherein said two guider ends are slidably fitted in said two guiding slots respectively so as to enable said control nut to slide axially within said valve body;

whereby by means of said magnetic controller, said magnet rotor is able to be driven to rotate in one direction, said rotating magnet rotor driving said actuation axle to rotate so as to drive said thread portion of said actuation axle to move axially towards said distal end, so that said valve member is pulled by said actuation axle to shut off said valve opening to close said valve body, furthermore when said magnet rotor is driven by said magnetic controller to rotate in opposite direction, said rotating magnet rotor drives said actuation axle to rotate to drive said thread portion of said actuation axle to move axially towards said proximal end, so that said valve member is pushed by said actuation axle to move away from said valve opening to open said valve body.

8. A magnetic actuation urethral valve, as recited in claim 7, wherein said actuation device further comprises a manual switch axle distally extended from said magnet rotor towards said exit opening to connect with a switch button.

9. A magnetic actuation urethral valve, as recited in claim 8, wherein said valve member comprises a valve head having a step hole therein, a head nut disposed within said step hole for tightly screwed onto said first end of said actuation axle, and a head cover covering said step hole by screwing therein, thus allowing said actuation axle to rotate inside said valve member freely.

10. A magnetic actuation urethral valve, as recited in claim 7, wherein said valve member comprises a valve head having a step hole therein, a head nut disposed within said step hole for tightly screwed onto said first end of said actuation axle, and a head cover covering said step hole by screwing therein, thus allowing said actuation axle to rotate inside said valve member freely.

11. A magnetic actuation urethral valve, comprising:

a valve member:

a valve body having a valve opening at a proximal end thereof and an exit opening at a distal end thereof, wherein said valve opening has a size smaller than a size of said valve member so as to enable said valve member sitting on said valve opening to shut off said valve body, wherein said valve body comprises a valve housing, a connecting sleeve, a valve seat, a retainer bearing, and a cover cap, said valve housing having an interior chamber, said connecting sleeve connecting to a proximal end of said valve housing, and a ring shaped supporting shoulder radially and inwardly extended from a bottom end thereof, said valve seat which has a U-shaped cross section is coaxially connected to said connecting sleeve, said valve seat having a center hole functioned as said valve opening, said retainer bearing being affixed at a distal end portion of said valve housing, a plurality of urine holes being formed on said retainer bearing, said cover cap being secured to a distal end of said valve housing and having has a central opening functioned as said exit opening, wherein said valve housing has a wavy exterior surface for more firmly mounting within a urethra; and an actuation device for selectively spacing out said valve member and said valve body from each other, wherein said actuation device comprises a control nut, a magnet rotor rotatably disposed inside said interior chamber of said valve housing of said valve body and adapted to be driven to rotate by a magnetic controller, and an actuation axle having a first end penetrating through said valve opening and connecting to said valve member and a second end coaxially connected to said magnet rotor; wherein said control nut is positioned between said valve opening and said magnet rotor and has a central threaded hole so as to enable said actuation axle to penetrate therethrough, and that said actuation axle has a threaded portion adapted for screwing with said thread hole, wherein said actuation device further comprises a first spring and a second spring which maintain certain pressures between said valve member and said valve seat as well as control movement of said control nut, and a guiding sleeve fittingly installed within said connecting sleeve and supported by said supporting shoulder, wherein two opposing guiding slots are longitudinally formed on said guiding sleeve, said control nut having two guider ends projected from two ends thereof, wherein said two guider ends are slidably fitted in said two guiding slots respectively so as to enable said control nut to slide axially within said guiding sleeve;

whereby by means of said magnetic controller, said magnet rotor is able to be driven to rotate in one direction, said rotating magnet rotor driving said actuation axle to rotate so as to drive said thread portion of said actuation axle to move axially towards said distal end, so that said valve member is pulled by said actuation axle to shut off said valve opening to close said valve body, furthermore when said magnet rotor is driven by said magnetic controller to rotate in opposite direction, said rotating magnet rotor drives said actuation axle to rotate to drive said thread portion of said actuation axle to move axially towards said proximal end, so that said valve member is pushed by said actuation axle to move away from said valve opening to open said valve body.

12. A magnetic actuation urethral valve, as recited in claim 11, wherein said actuation device further comprising a manual switch axle distally extended from said magnet rotor towards said exit opening to connect with a switch button, wherein said retainer bearing has a center hole to enable said switch axle rotatably passing through, and said switch button is extended below said retaining bearing for pushing said valve member upwards to open said valve opening with a catheter or the like.

13. A magnetic actuation urethral valve, as recited in claim 12, wherein said valve member comprises a valve head having a step hole therein, a head nut disposed within said step hole for tightly screwed onto said first end of said actuation axle, and a head cover covering said step hole by screwing therein, thus allowing said actuation axle to rotate inside said valve member freely.

14. A magnetic actuation urethral valve, as recited in claim 11, wherein said valve member comprises a valve head having a step hole therein, a head nut disposed within said step hole for tightly screwed onto said first end of said actuation axle, and a head cover covering said step hole by screwing therein, thus allowing said actuation axle to rotate inside said valve member freely.

* * * * *